(12) United States Patent
Thakur (10) Patent No.: US 11,351,278 B1
(45) Date of Patent: Jun. 7, 2022

(54) SELF-STERILIZING IV POLE SYSTEM (71) Applicant: Vishal Thakur, Springfield, NJ (US)

(72) Inventor: Vishal Thakur, Springfield, NJ (US)

(*) Notice: Subject to any disclaimer, the term of this patent is extended or adjusted under 35 U.S.C. 154(b) by 413 days.

(21) Appl. No.: 16/562,768

(22) Filed: Sep. 6, 2019

Related U.S. Application Data (60) Provisional application No. 62/728,476, filed on Sep. 7, 2018.

(51) Int. Cl.
| | |
|---|---|
| A61L 2/10 | (2006.01) |
| F21S 4/20 | (2016.01) |
| H01R 13/62 | (2006.01) |
| H01R 43/26 | (2006.01) |
| A61L 2/26 | (2006.01) |
| F21V 23/00 | (2015.01) |
| F21Y 115/10 | (2016.01) |
| F21Y 105/10 | (2016.01) |

(52) U.S. Cl.
CPC ............... *A61L 2/10* (2013.01); *A61L 2/26* (2013.01); *F21S 4/20* (2016.01); *F21V 23/001* (2013.01); *H01R 13/6205* (2013.01); *H01R 43/26* (2013.01); *A61L 2202/11* (2013.01); *A61L 2202/16* (2013.01); *F21Y 2105/10* (2016.08); *F21Y 2115/10* (2016.08)

(58) Field of Classification Search
CPC ........... A61L 2/10; F21S 4/20; H01R 13/6205
See application file for complete search history.

(56) References Cited

U.S. PATENT DOCUMENTS

| | | | |
|---|---|---|---|
| 8,747,764 B1 | 6/2014 | Burchman et al. | |
| 9,198,990 B2 | 12/2015 | Fletcher | |
| 9,295,743 B2 | 3/2016 | Gomez | |
| 9,597,243 B1 | 3/2017 | Helmick et al. | |
| 9,622,911 B2 | 4/2017 | Rubinfeld et al. | |
| 2008/0116157 A1 | 5/2008 | Fulbrook et al. | |
| 2015/0205985 A1 | 7/2015 | Jinadatha | |
| 2015/0335774 A1* | 11/2015 | Gomez | ........... A61L 2/10 250/454.11 |
| 2017/0340760 A1 | 11/2017 | Starkweather et al. | |
| 2019/0240369 A1* | 8/2019 | Rotelli | ........... A61L 2/10 |

FOREIGN PATENT DOCUMENTS

| | | |
|---|---|---|
| CN | 203235082 U | 10/2013 |
| CN | 105537086 A | 5/2016 |
| WO | 2010060079 A1 | 5/2010 |
| WO | 2018013581 A1 | 1/2018 |

OTHER PUBLICATIONS

Anonymous, neoBLUE LED Phototherapy Systems, ParagonCare, Jun. 27, 2018, https://www.paragoncare.com.au/products/neoblue-led-phototherapy-systems/.

* cited by examiner

*Primary Examiner* — Kevin Joyner
(74) *Attorney, Agent, or Firm* — Werschulz Patent Law, LLC; Patricia P. Werschulz, Esq.

(57) ABSTRACT

A system and method for sterilizing a wheelchair, stretcher or the like, that comprises an intravenous (IV) pole attaching to the wheelchair or stretcher having an electrical connector at the pole top, and a reflective drape having an interior lined with UV LED lights that electrically connects to the connector on top of the IV pole when draped over the wheelchair or stretcher. The UV LED lights sterilize the wheelchair or other equipment that is under the drape after a period of exposure to UV radiation without using disinfectant chemical sprays or wiping with disinfectant cloths and without staff attention.

20 Claims, 7 Drawing Sheets

SELF-STERILIZING IV POLE SYSTEM

CROSS-REFERENCE TO RELATED APPLICATIONS

This application is a nonprovisional utility application of the provisional patent application, Ser. No. 62/728,476 filed in the United States Patent Office on Sep. 7, 2018, and claims the priority thereof and is expressly incorporated herein by reference in its entirety.

TECHNICAL FIELD

The present disclosure relates generally to a self-sterilizing IV pole system. More particularly, the present disclosure relates to a system comprising a self-sterilizing IV pole with a drape for attaching to wheelchair or gurney that sterilizes the IV pole as well as the wheelchair or gurney.

BACKGROUND

In many health care facilities, from the largest hospitals to small assisted living and residential institutions, patients spend many hours in wheelchairs. Often IV (intra-venous) poles are attached to the wheelchairs so that drugs, vital fluids and nutritional liquids can be provided intravenously. These chairs and IV poles must be routinely cleaned and sanitized to prevent spreading infections among patients who may be already immune compromised.

Other types of equipment used in these settings such as beds, gurneys and the like generally are equipped to hold IV poles. All this equipment requires cleaning, sanitizing and sterilization to minimize the transfer of hospital-acquired or nosocomial infections that happen in health care institutions.

Cleaning, sanitizing and sterilizing equipment is time-consuming and takes time away from providing direct patient care. Failure to properly execute the cleaning, sanitizing and sterilizing protocol can result in a catastrophic spread of infection within the institution.

The protocol generally involves spraying strong disinfectant solutions, possibly in combination with steam and high pressure to penetrate all the crevices, openings and generally inaccessible areas. The chair is wiped down and allowed to dry. The strong solutions cause the vinyl or leather covered parts to deteriorate and crack, the cracks providing opportunities for bacteria to invade into seat and back cushions. The process is time-consuming and takes caregivers away from providing direct to patient care.

While these methods may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide sterilized equipment for use in a hospital, assisted living or residential institution. Accordingly, an aspect of an example embodiment in the present disclosure provides an efficient and easy-to-use system and method for sterilizing equipment such as wheelchairs and stretchers for use in a hospital, assisted living, or residential institution.

A further aspect of an example embodiment in the present disclosure is to provide sterilized equipment for use in a hospital, assisted living or residential institution that minimizes staff time spent in the sterilization process. Accordingly, an aspect of an example embodiment in the present disclosure provides an efficient and easy to use system and method for sterilizing equipment that is quickly setup and sterilizes equipment without direct staff involvement.

Another aspect of an example embodiment in the present disclosure is to provide a sterilization system that is adaptable to wheelchair or stretcher without excessive wiping and scrubbing. Accordingly, the present disclosure provides a sterilization system that includes an intravenous (IV) pole connecting to a reflective drape with interior UV (ultraviolet) LED (Light-Emitting Diode) lights at a wavelength that kills microorganisms that covers the equipment providing sufficient UV radiation for killing microorganisms.

Accordingly, the present disclosure describes a system and method for sterilizing a wheelchair or stretcher that comprises an intravenous (IV) pole attaching to the wheelchair or stretcher having an electrical connector at the pole top, and a reflective drape having an interior lined with UV LED lights that electrically connect to the connector on top of the IV pole when draped over the wheelchair or stretcher. The UV LED lights sterilize the wheelchair or stretcher that is under the drape after a period of exposure to UV radiation without using disinfectant chemical sprays or wiping with disinfectant cloths and without staff attention.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
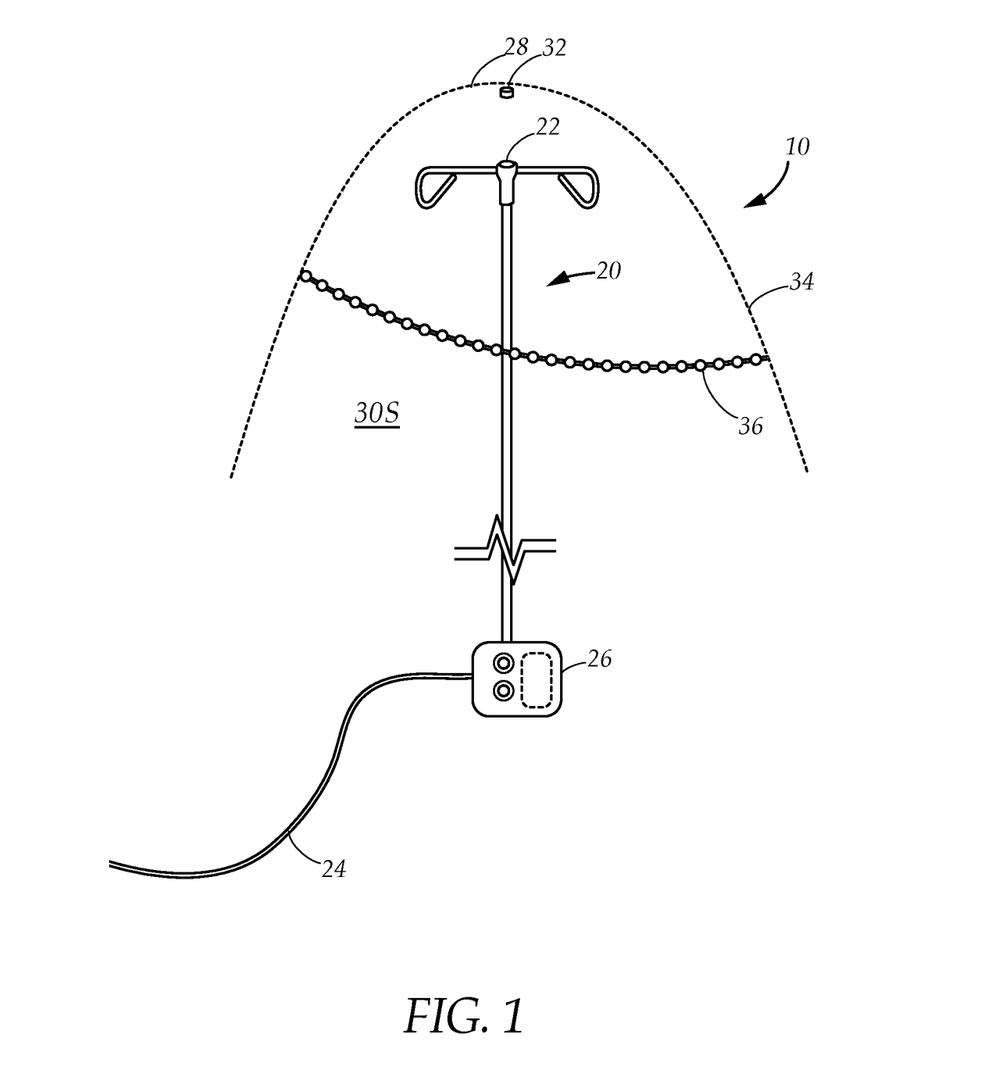
FIG. 1 is a front elevational view of an inside of an example embodiment of a self-sterilizing intravenous (IV) pole system.

FIG. 1. illustrates an example embodiment of a self-sterilizing intravenous (IV) pole system 10. The system comprises an intravenous (IV) pole 20 and a sterilization drape 30. The drape 30 generally is a conical shape made from flexible material so that when held at an apex 28, the drape loosely enshrouds any irregularly shaped object such as a wheelchair or stretcher underneath.

In the following disclosure, a wheelchair is provided as an example of patient equipment that can be sterilized in this system, but it is understood that the system can be used to provide sterilization for stretchers, gurneys, hospital beds and the like and is not limited to wheelchairs. Any hospital or institutional equipment configured for attaching an IV pole and configured to be covered by a drape is envisioned within the inventive concept.

The drape 30 has an interior surface 30S that is reflective, which cannot be shown in the drawings.

The drape has a plurality of LEDs (light-emitting diodes) on LED strips 36 on the interior surface 30S and a plurality of LED wiring 34 on the interior surface 30S, the LED wiring 34 in electrical communication with the LED strips 36 and a disk connector 32. The disk connector 32 is at the apex 28 of the drape 30 and is in electrical communication with the LED strips 36 through the LED wiring 34.

In one example embodiment, a thin transparent layer of plastic may line the interior surface 30S to protect the LED wiring 34 and the LED strips 36.

Figure 2:
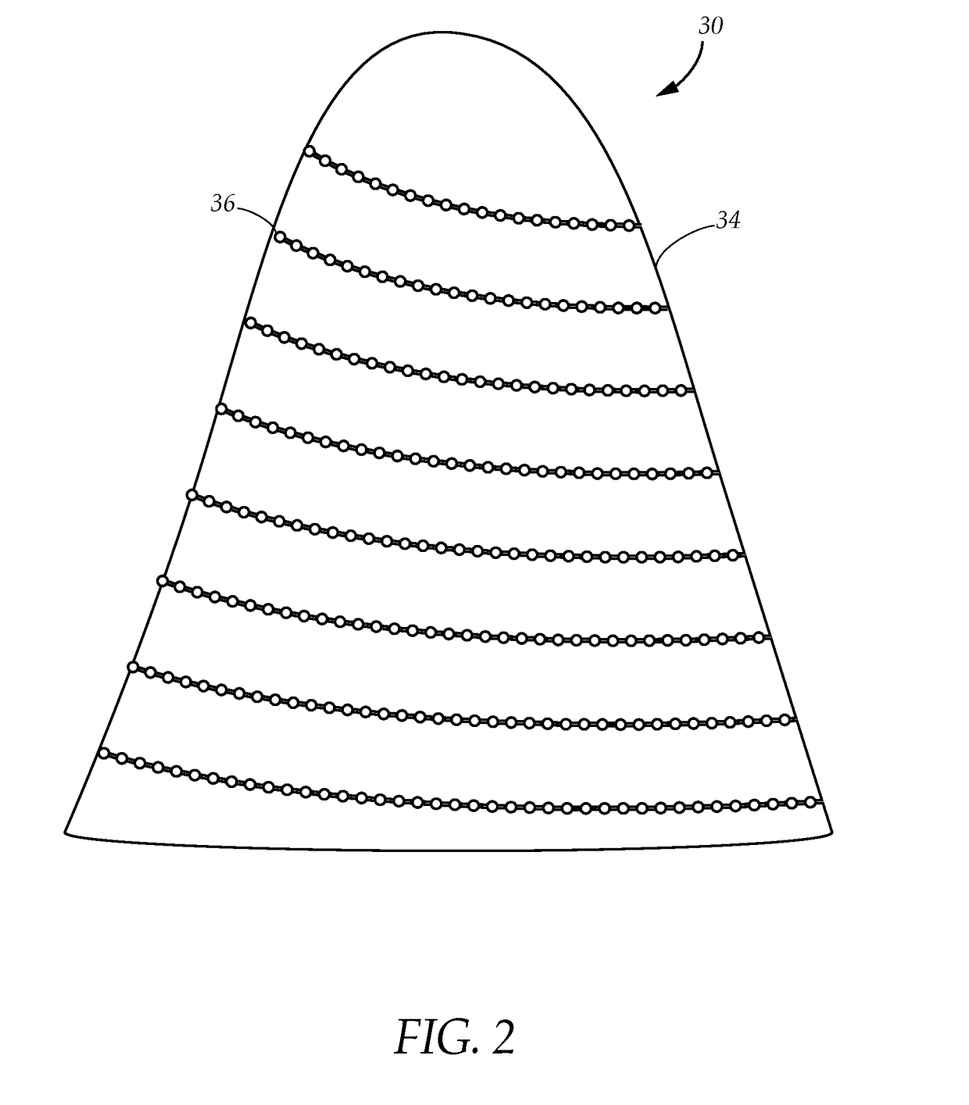
FIG. 2 is a front elevational view of the inside of an example embodiment of a drape of a self-sterilizing IV pole system showing a first pattern of light distribution of a plurality of LED (light-emitting diode) strips.
Figure 3:
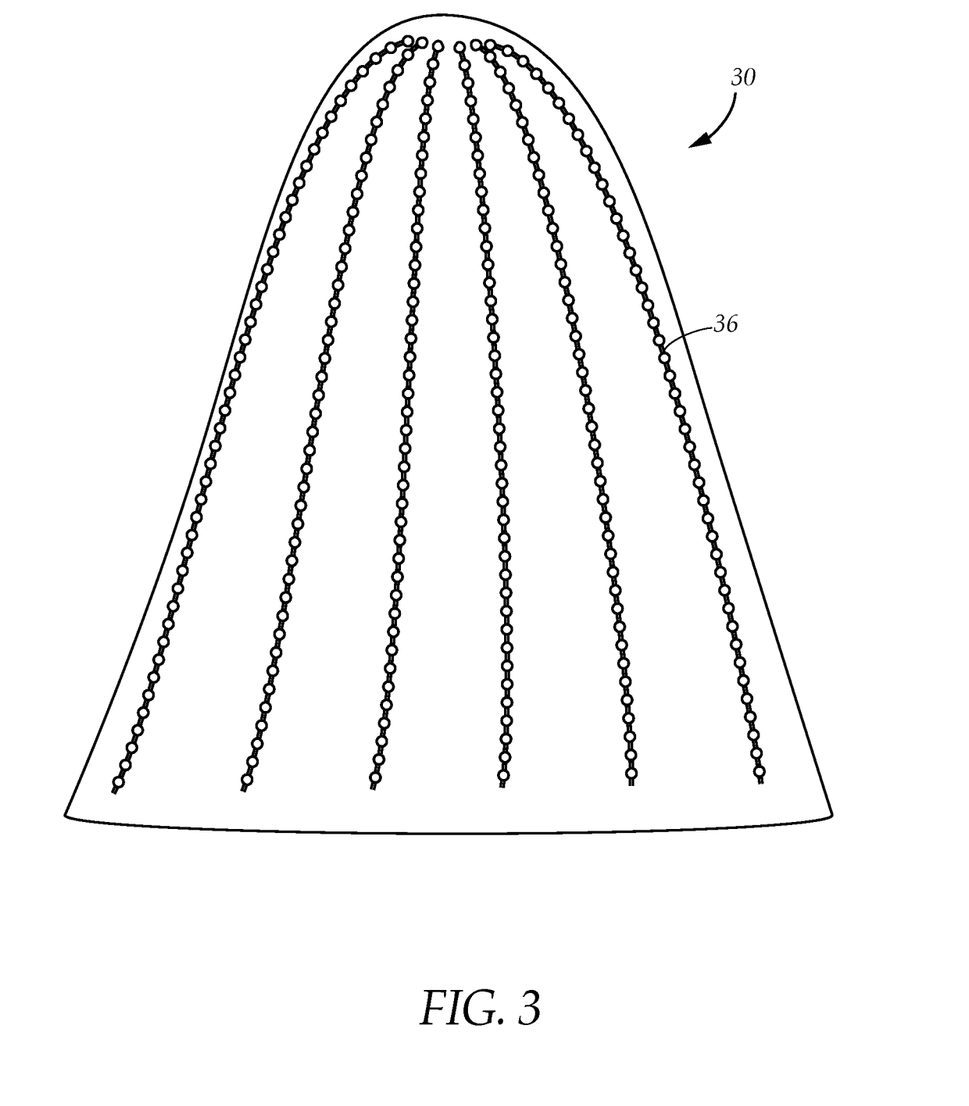
FIG. 3 is a front elevational view of the inside of an example embodiment of a drape of a self-sterilizing IV pole system showing a second pattern of light distribution of the LED strips.
Figure 4:
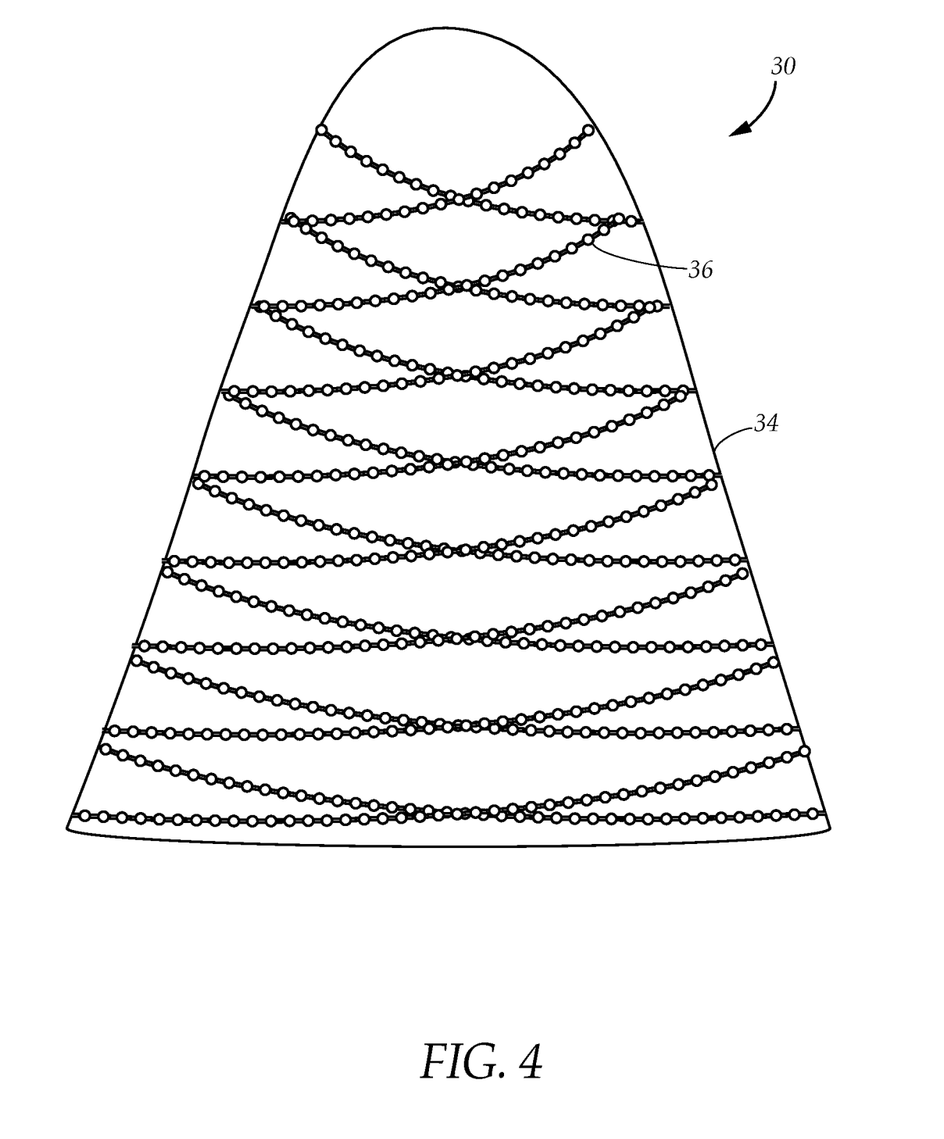
FIG. 4 is a front elevational view of the inside of an example embodiment of a drape of a self-sterilizing IV pole system showing a third pattern of light distribution of the plurality of LED strips.

FIGS. 2-4 demonstrate various configurations of LED strips 36 deployed on the interior surface 30S of the drape 30. The LED strips 36 are arrayed along a plurality of lines such that when the LED lights are lit, there are no dark areas inside the drape. In the illustrations, there are several patterns of LED lights shown, however these are not limitations and other patterns of LED strips 36 are possible within the inventive concept.

FIG. 2 shows a spiral pattern of LED strips 36, FIG. 3 a vertical cascade and FIG. 4 an intersecting grid pattern of deployment. In order to have a practical period of sterilization with minimal number of LED lights, a period of 30 minutes of sterilization was chosen to determine the number of LEDs. Calculations show that the maximum distance from a first LED light to a second LED light is 10 cm. A distance between a first UV-C LED light and a second UV-C LED light is equal to or less than 10 cm is preferable. A 10 cm by 10 cm grid pattern of LED strips 36 having at least 100 LEDs on the interior surface can achieve 99.9% effective sterilization. The interior surface 30S of the drape 30 should no greater distance from a surface to be sterilized than approximately than 30 cm.

The LED lights are ultraviolet (UV-C LED) lamps that emit UV light at selectable wavelengths between 255 and 280 nm encompassing 270 nm, which is the optimal wavelength for killing microorganisms. The intensity of the UV-C LED must be minimally 12 mW, preferably between 20 mW and 25 mW. Experiments were performed with the LED light source at 1 foot or approximately 30 cm from inoculated dishes that had been previously incubated at standard conditions. A distance equal to or less than 30 cm is preferable. Generally, even at a low power such as 12 mW UV-C lights were effective after 30 minutes exposure. Doubling the intensity provides a high probability of a kill at 99.9% level.

The effectiveness of 12 mW against common pathogens is in Table 1.

TABLE 1

| TIME | E. Coli | S. Aureus | P. Aeruginosa |
| --- | --- | --- | --- |
| 10 min | 0 | several | 14 |
| 30 min | 0 | 0 | 2 |
| 50 min | 0 | 0 | 9 |

The UV radiation generated by these LEDs is able to eliminate over 99.9% of microorganisms. In one embodiment, a sufficiently large number of LEDs such as a non-limiting example of one hundred (100), which provides sterilization of a wheelchair with a sterilization time of a minimum of 30 minutes. As a non-limiting example, a 10 cm by 10 cm grid array of the 100 LEDs inside the drape 30 is effective in around 30 minutes, assuming wheelchair has total surface area of 10.00 $cm^2$. To decrease the sterilization time, more LEDs can be added or alternatively, larger surface areas can be sterilized within 30 minutes by increasing the size of the drape and the number of LEDs. The UV conical drape 30 is especially unique because it utilizes a connection point at the tip of the IV pole 20.

Returning to FIG. 1, the IV pole 20 is telescopic in one example embodiment. Further, the IV pole is hollow and has electric wiring (not shown) running throughout a length of the IV pole 20, the wiring connecting to a power supply 26. In one example embodiment, the power supply 26 is an AC-DC adaptor that further connects to a power cord for plugging into electrical current via a simple 60$v$ outlet plug that hangs from the bottom of the IV pole 20. In another example embodiment, the power supply 26 connects is a battery power source.

The wiring connects to a top disk connector 22 which is joined to a top of the IV pole 20.

Figure 1A:
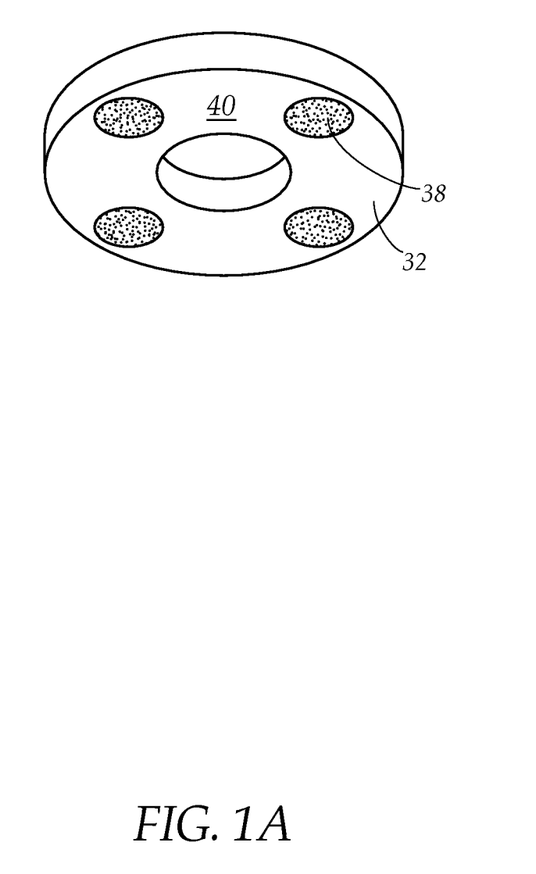
FIG. 1A is a perspective view of a disk connector in the example embodiment of a self-sterilizing intravenous (IV) pole system.
Figure 1B:
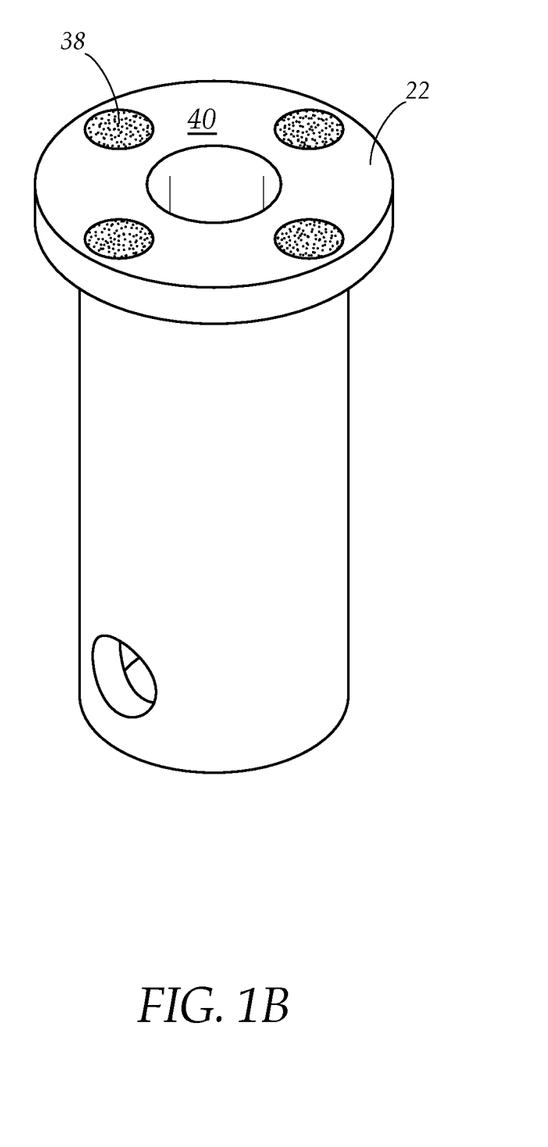
FIG. 1B is a perspective view of a top disk connector in the example embodiment of a self-sterilizing intravenous (IV) pole system.

Referring to FIG. 1B, the top disk connector 22 has copper plates 40 to conduct the electrical currents across a top surface of the top disk connector.

The top disk connector has a plurality of magnets 38 within the copper plates 40. Similarly, as shown in FIG. 1A, the disk connector 32 of the conical drape 30 has copper plates 40 with a plurality of magnets 38. The magnets 38 align the top disk connector 22 of the IV pole to the disk connector 32 of the conical drape, creating and securing sufficient contact for current to flow.

Figure 5:
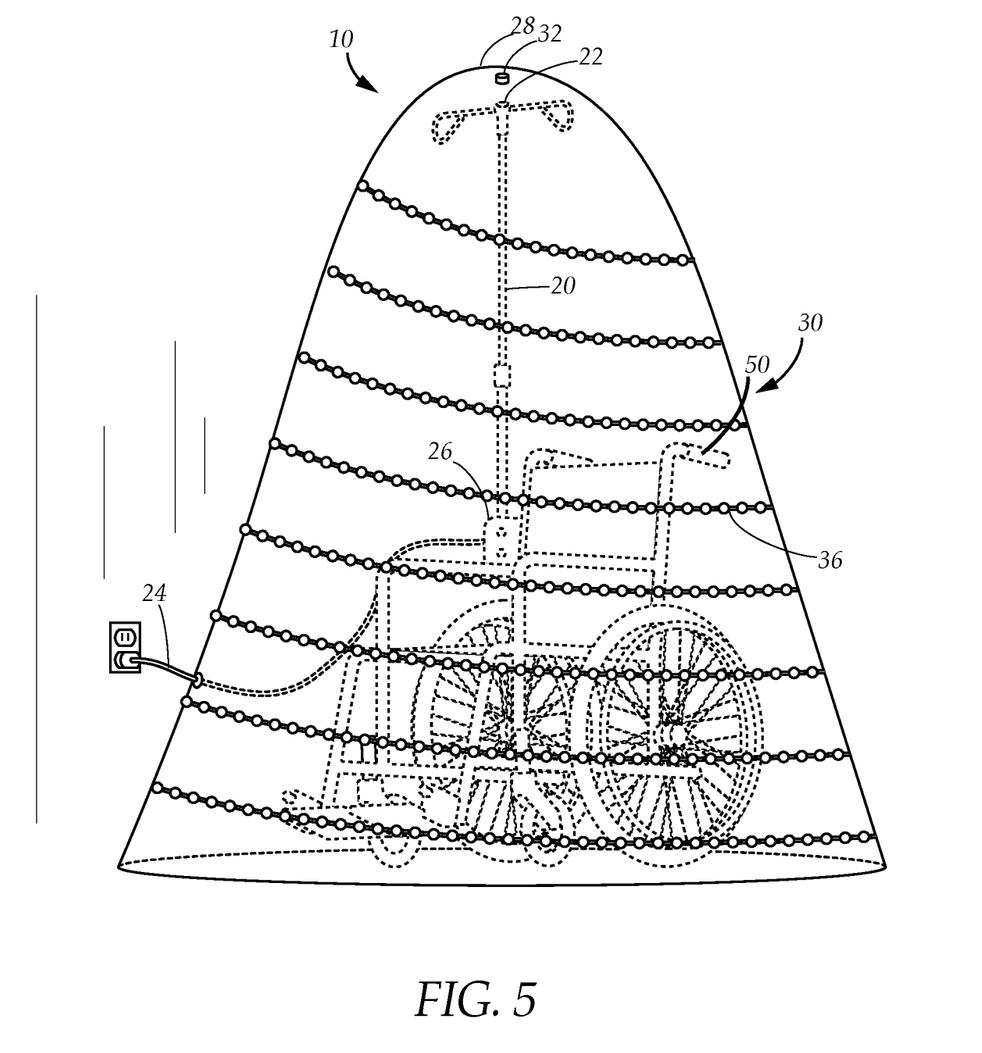
FIG. 5 is a front elevational view of the example embodiment of the self-sterilizing IV pole system engaging a wheelchair.

In FIG. 5, a method of using the system 10 is illustrated. The method comprises placing a conical drape 30 having a disk connector 32 at the apex 28 of the conical drape 30, the interior having a plurality of UV (ultra-violet) LED (light-emitting diodes) light strips 36 deployed on the interior of the conical drape 30 in electrical communication with the disk connector, the conical drape placing over a hollow IV pole 20 attached to a wheelchair 50, the hollow IV pole having a top disk connector 22 in electrical communication with electrical wiring inside the hollow IV pole 20.

The next step is contacting the disk connector 32 at the apex 28 of the conical drape 30 to the top disk connector 22 of the IV pole 20 creating electrical communication between the electrical wiring of the IV pole 20 and the UV LED light strips 36 on the interior of the conical drape 30, followed by connecting the electrical wiring of the IV pole 20 to a power source 24. After a minimum of 30 (thirty) minutes, the electrical wiring of the IV pole 20 is disconnected from the power source 24 and the conical drape 30 is removed from the wheelchair 50.

The disk connector 32 of the conical drape 30 and the top disk connector 22 of the IV pole 20 each have a plurality of magnets 38 as shown in FIGS. 1A and 1B, and the step of contacting the disk connector 32 at the apex 28 of the conical drape 30 to the top disk connector 22 of the IV pole 20 further comprises aligning the plurality of magnets 38 of the disk connector of the conical drape and with the plurality of magnets 38 of the top disk connector of the IV pole 20.

If the wheelchair has a generic UV pole or none at all, the method is preceded by the step of attaching the UV pole of the system 10 to the wheelchair.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a self-sterilizing UV pole system. The disclosure is illustrated by example in the drawing figures, and throughout the written description. It should be understood that numerous variations are possible, while adhering to the inventive concept. Such variations are contemplated as being a part of the present disclosure.

The invention claimed is:

1. A self-sterilizing IV (intravenous) pole system for sterilizing wheelchairs, comprising:
   a hollow IV (intravenous) pole configured for attaching to a wheelchair, the hollow IV pole having a top disk connector in electrical communication with electrical wiring inside the hollow IV pole;
   a conical drape having an apex and an interior, the apex having a disk connector in electrical communication with the top disk connector of the hollow IV pole; and
   a plurality of UV (ultra-violet) LED (light-emitting diodes) light strips deployed on the interior of the conical drape in electrical communication with the disk connector at the apex of the conical drape.

2. The system as described in claim 1, further comprising a plurality of magnets on the disk connector of the IV pole and a plurality of magnets on the disk connector at the apex of the conical drape.

3. The system as described in claim 2, wherein the plurality of magnets on the disk connector of the IV pole align with the plurality of magnets on the disk connector of the apex of the conical drape thereby creating and securing electrical communication between the disk connector of the IV pole and the disk connector of the conical drape.

4. The system as described in claim 3, wherein the drape has an interior surface and a plurality of LED wiring on the interior surface.

5. The system as described in claim 4, wherein the LED wiring is in electrical communication with the LED strips and the disk connector at the apex of the conical drape thereby placing the LED strips in electrical communication with the disk connector at the apex of the conical drape.

6. The system as described in claim 5, wherein the LED light strips further comprise a plurality of UV-C LED lights.

7. The system as described in claim 6, wherein a distance between a first UV-C LED light and a second UV-C LED light is equal to or less than 10 cm.

8. The system as described in claim 7, wherein the LED light strips are deployed in a grid pattern.

9. The system as described in claim 8, wherein a distance between the LED light strips and a surface of the wheelchair is equal to or less than 30 cm.

10. A self-sterilizing IV (intravenous) pole system for sterilizing wheelchairs, comprising:
- a conical drape having an apex and a reflective interior, the reflective interior having a plurality of UV (ultra-violet) LED (light-emitting diodes) light strips deployed on the reflective interior of the conical drape in a grid pattern, the UV LED light strips in electrical communication with a disk connector at the apex of the conical drape; and
- a hollow IV (intravenous) pole configured for attaching to a wheelchair, the hollow IV pole having electrical wiring inside the hollow IV pole, the electrical wiring configured for connecting to a power supply.

11. The system as described in claim 10, wherein the LED light strips further comprise a plurality of UV-C LED lights.

12. The system as described in claim 11, wherein a distance between a first UV-C LED light in the grid pattern and a second UV-C LED light in the grid pattern is equal to or less than 10 cm.

13. The system as described in claim 12, wherein a distance between the LED light strips and a surface of the wheelchair is equal to or less than 30 cm.

14. The system as described in claim 13, wherein the hollow IV pole has a top and a top disk connector on the hollow IV pole top in electrical communication with the electrical wiring inside the hollow IV pole.

15. The system as described in claim 14, further comprising a plurality of magnets on the top disk connector of the IV pole and a plurality of magnets on the disk connector of the conical drape.

16. The system as described in claim 15, wherein the plurality of magnets on the disk connector of the IV pole align with the plurality of magnets on the disk connector of the conical drape thereby creating and securing electrical communication between the disk connector of the IV pole and the disk connector of the conical drape.

17. The system as described in claim 16, wherein the LED wiring is in electrical communication with the LED strips and the disk connector at the apex of the conical drape thereby placing the LED strips in electrical communication with the disk connector at the apex of the conical drape.

18. A method for sterilizing a wheelchair, comprising:
- placing a conical drape having an interior, the interior having a disk connector at an apex of the conical drape, the interior having a plurality of UV (ultra-violet) LED (light-emitting diodes) light strips deployed on the interior of the conical drape in electrical communication with the disk connector, the conical drape placing over a hollow IV (intravenous) pole attached to a wheelchair, the hollow IV pole having a top disk connector in electrical communication with electrical wiring inside the hollow IV pole;
- contacting the disk connector at the apex of the conical drape to the top disk connector of the IV pole creating electrical communication between the electrical wiring of the IV pole and the UV LED light strips on the interior of the conical drape;
- connecting the electrical wiring of the IV pole to a power source; and
- disconnecting the electrical wiring of the IV pole from the power source and removing the conical drape from the wheelchair after a minimum of thirty (30) minutes.

19. The method as described in claim 18, wherein the step of placing the conical drape over the hollow IV pole is preceded by the step of attaching the hollow IV pole to the wheelchair.

20. The method as described in claim 18, wherein the disk connector of the conical drape and the top disk connector of the IV pole each have a plurality of magnets and the step of contacting the disk connector at the apex of the conical drape to the top disk connector of the IV pole further comprises aligning the plurality of magnets of the disk connector of the conical drape and with the plurality of magnets of the top disk connector of the IV pole.

\* \* \* \* \*